(12) United States Patent  
Seino

(10) Patent No.: US 7,557,252 B2  
(45) Date of Patent: Jul. 7, 2009

(54) PROCESS FOR PRODUCING DIHYDROXYBENZENE AND DIISOPROPYLBENZENDICARBINOL

(75) Inventor: Mamoru Seino, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/673,786

(22) Filed: Feb. 12, 2007

(65) Prior Publication Data

US 2007/0197838 A1 Aug. 23, 2007

(30) Foreign Application Priority Data

Feb. 17, 2006 (JP) .............................. 2006-040383

(51) Int. Cl.  
   *C07C 37/00* (2006.01)
(52) U.S. Cl. ...................................................... 568/771
(58) Field of Classification Search .................. 568/771  
   See application file for complete search history.

(56) References Cited

U.S. PATENT DOCUMENTS 6,350,921 B1 2/2002 Durairaj et al.

FOREIGN PATENT DOCUMENTS

JP 09-143112 * 6/1997

* cited by examiner

*Primary Examiner*—Daniel M Sullivan  
*Assistant Examiner*—Kellette Gale  
(74) *Attorney, Agent, or Firm*—Sughrue Mion, PLLC

(57) ABSTRACT

A process for simultaneously producing a dihydroxybenzene and a diisopropylbenzene dicarbinol, which contains subjecting a diisopropylbenzene with an oxygen containing gas to obtain an oxidation reaction mixture containing a diisopropylbenzene dihydroperoxide and a diisopropylbenzene hydroxy hydroperoxide followed by an extraction separation step, a decomposition step, a distillation separation step, a reduction step and a post-treatment step in this order, the process containing purifying the diisopropylbenzene dicarbinol from the liquid containing the diisopropylbenzene dicarbinol obtained in the reduction step through purification operations containing crystallization, filtration and subsequent drying, and supplying a filtrate obtained by the filtration to the decomposition step and/or distillation separation step.

6 Claims, 2 Drawing Sheets

PROCESS FOR PRODUCING DIHYDROXYBENZENE AND DIISOPROPYLBENZENDICARBINOL

BACKGROUND OF THE INVENTION

1. Field of the Invention

The present invention relates to a process for producing a dihydroxybenzene and a diisopropylbenzene dicarbinol. More particularly, the present invention relates to a process for simultaneously producing dihydroxybenzene and diisopropylbenzene dicarbinol using a diisopropylbenzene as a raw material, which has an excellent effect such that a filtrate generated with production of diisopropylbenzene dicarbinol, can be efficiently treated.

2. Description of the Related Art

There is publicly known a process for simultaneously producing dihydroxybenzene and diisopropylbenzene dicarbinol using diisopropylbenzene as a raw material (JP 9-143112 A).

Herein, in a filtration step of diisopropylbenzene dicarbinol, a treatment of a filtrate generated is required. As the treatment of the filtrate, it is disposed as a waste oil as it is or a waste oil after recovering effective ingredients contained in the filtrate. But, there is a problem that the recovery of effective ingredients is expensive for the equipment.

SUMMARY OF THE INVENTION

Under such situations, an object of the present invention is to provide a process for simultaneously producing dihydroxybenzene and diisopropylbenzene dicarbinol using diisopropylbenzene as a raw material, which has an excellent effect such that the filtrate generated with production of diisopropylbenzene dicarbinol, can be efficiently treated.

Namely, the present invention relates to a process for simultaneously producing a dihydroxybenzene and a diisopropylbenzene dicarbinol, which comprises the following steps of:

(1) oxidizing a diisopropylbenzene with an oxygen-containing gas to obtain an oxidation reaction mixture containing a diisopropylbenzene dihydroperoxide and a diisopropylbenzene hydroxy hydroperoxide;

(2) subjecting the oxidation reaction mixture obtained in the oxidation step (1) to extraction operation with an alkaline aqueous solution and subsequently to extraction operation with an organic solvent to separate into a liquid containing the diisopropylbenzene dihydroperoxide and a liquid containing the diisopropylbenzene hydroxy hydroperoxide;

(3) subjecting the liquid containing the diisopropylbenzene dihydroperoxide to decomposition reaction in the presence of an acid catalyst to obtain a liquid containing a dihydroxybenzene;

(4) subjecting the liquid containing the diisopropylbenzene hydroxy hydroperoxide to decomposition reaction in the presence of an acid catalyst to obtain a liquid containing acetone and an isopropenyl phenol;

(5) subjecting the liquid containing the isopropenyl phenol and acetone to distillation to separate it into a mixture of acetone and the organic solvent, and a heavy fraction containing the isopropenyl phenol;

(6) subjecting a part of the diisopropylbenzene hydroxy hydroperoxide to reduction reaction to obtain a liquid containing a diisopropylbenzene dicarbinol, and (7) purifying the diisopropylbenzene dicarbinol from the liquid containing the diisopropylbenzene dicarbinol through purification operation containing crystallization, filtration and subsequent drying, and supplying a filtrate obtained by the filtration to the decomposition step (4) and/or distillation step (5).

DETAILED DESCRIPTION OF THE INVENTION

Figure 1:
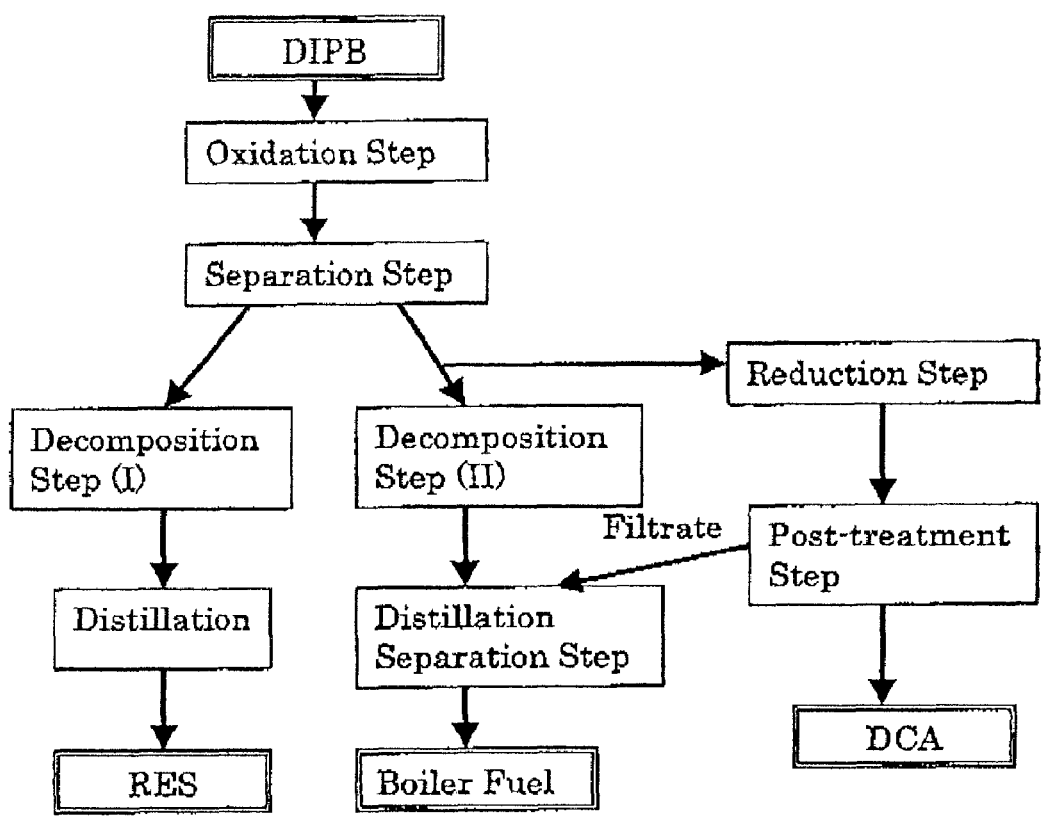
FIG. 1 shows a schematic view of one embodiment of the present invention.
Figure 2:
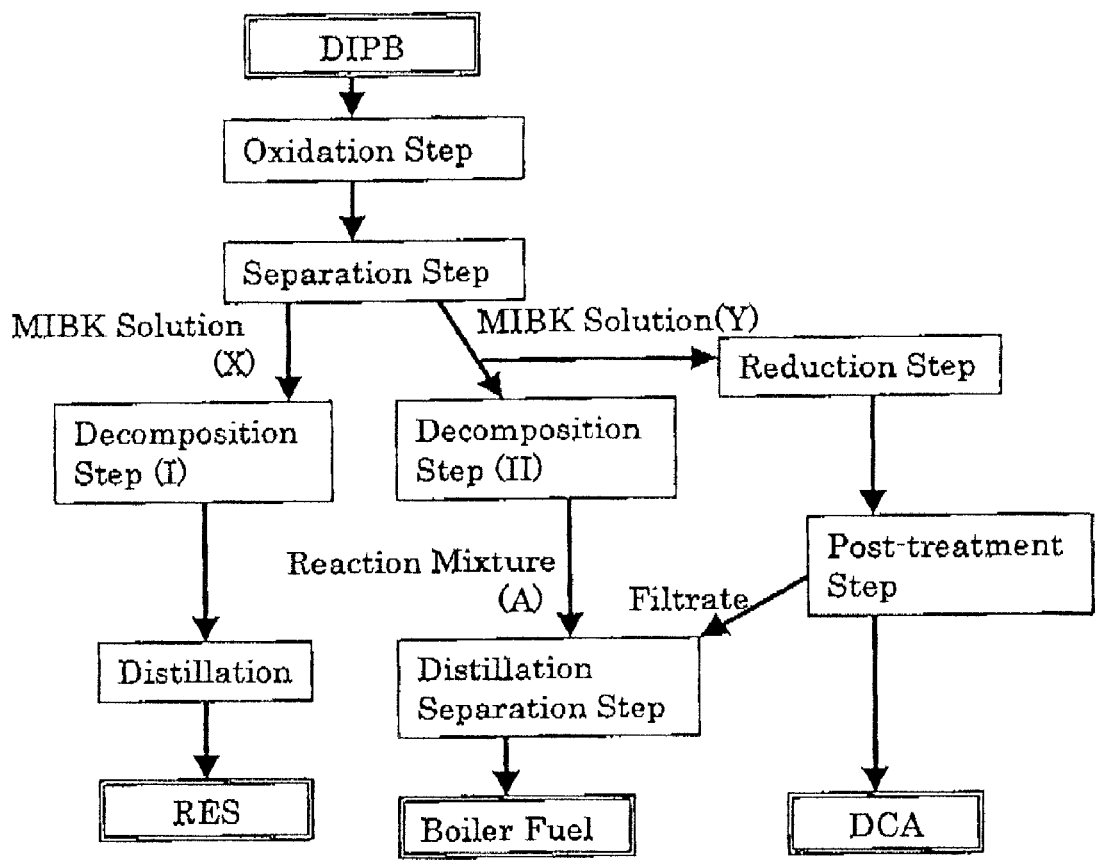
FIG. 2 shows a schematic view corresponding to Example 1.

In the present invention, a dihydroxybenzene and a diisopropylbenzene dicarbinol are simultaneously produced from a diisopropylbenzene as a raw material. Specific examples thereof include a case of which the diisopropylbenzene is m-diisopropylbenzene and/or p-diisopropylbenzene, the dihydroxybenzene is resorcinol and/or hydroquinone and the diisopropylbenzene dicarbinol is m-diisopropylbenzene dicarbinol and/or p-diisopropylbenzene dicarbinol, and preferably, a case of which the diisopropylbenzene is m-diisopropylbenzene, the dihydroxybenzene is resorcinol and the diisopropylbenzene dicarbinol is m-diisopropylbenzene dicarbinol.

The oxidation step (1) in the present invention is a step for obtaining the oxidation reaction mixture containing a diisopropylbenzene hydroperoxide (herein-after, referred to as "MHPO"), a diisopropylbenzene dihydroperoxide (herein-after, referred to as "DHPO") and a diisopropylbenzene hydroxy hydroperoxide (herein-after, referred to as "CHPO") by subjecting a diisopropylbenzene (herein-after, referred to as "DIPB") to oxidation reaction with an oxygen-containing gas.

The following apparatus and conditions for conducting the oxidation step, are exemplified.

The oxidation step (1) is a step of oxidizing a raw material liquid with an oxygen-containing gas such as air or a dilute oxygen in which is diluted with an inert gas such as nitrogen or argon. Air is preferably used.

The raw material liquid for oxidation usually contains 5% or less by weight of DHPO in addition to 20 to 60% by weight of MHPO and 10 to 40% by weight of DIPB as main raw materials. As usual reaction conditions, a temperature of 70 to 110° C., a pressure of 0 to 1 MPaG, a residence time of 0 to 50 hours and the like are illustrated. As an apparatus used in the oxidation step, for example, a continuous type or batch type reaction vessel or reaction column can be listed. The oxidation reaction mixture obtained in the oxidation step usually contains 3 to 30% by weight of DHPO, 20 to 60% by weight of MHPO and not more than 35% by weight of DIPB.

The extraction separation step (2) in the present invention is a step for separating DHPO and CHPO in the oxidation reaction mixture into a liquid containing DHPO and a liquid containing CHPO, respectively by subjecting the oxidation reaction mixture obtained in the oxidation step (1) to extraction operation with an alkaline aqueous solution and subsequent extraction operation with an organic solvent.

Specific examples of an alkali compound used in the alkaline aqueous solution, preferably include sodium hydroxide and potassium hydroxide, more preferably sodium hydroxide. Herein-after, a case of which the alkaline aqueous solution is a sodium hydroxide aqueous solution, is described, but the present invention is not restricted thereto.

The oxidation reaction mixture obtained in the oxidation step (1) is firstly subjected to extraction operation with a sodium hydroxide aqueous solution. The oxidation reaction mixture contains DIPB, MHPO, DHPO, CHPO, and further others as by products. Among these, DHPO and CHPO are extracted into the sodium hydroxide aqueous solution. In this case, a sodium hydroxide aqueous solution and/or DIPB in an appropriate amount may be added separately for heightening separability of oil and water and extraction efficiency.

The extraction temperature is usually 0 to 100° C. An organic layer containing DIPB and MHPO not extracted into the sodium hydroxide aqueous solution, can be recycle to the oxidation step. The concentration of sodium hydroxide in the sodium hydroxide aqueous solution used in the extraction of DHPO and MHPO is preferably 2 to 30% by weight, more preferably 4 to 15% by weight. When the concentration is lower than 2% by weight, the extraction efficiency may be lowered, on the other hand, the concentration of higher than 30% by weight may cause increase of the alkali amount used and degradation of the effective ingredients such as DHPO and CHPO.

A sodium hydroxide aqueous solution containing DHPO and CHPO obtained by extraction operation with the sodium hydroxide aqueous solution, is next subjected to extraction operation with an organic solvent. DHPO and CHPO can be separated by this operation, respectively.

The organic solvent used in the separation step (2), include preferably ketones having 4 to 10 carbon atoms, ethers having 4 to 10 carbon atoms and alcohols having 4 to 8 carbon atoms, and most preferably methylisobutylketone (herein-after, referred to as "MIBK"). The solvent may be used alone or as a mixture of two or more kinds.

The extraction with the organic solvent is conducted preferably in a combination of low temperature extraction of about 0 to about 50° C. with high temperature extraction of higher by 5 to 70° C. than the extraction temperature in the low temperature extraction. Namely, CHPO is selectively transferred to an organic solvent layer through the low temperature extraction, thereafter DHPO is transferred to an organic layer through the high temperature extraction. As the result, CHPO and DHPO are individually separated and separately recovered.

However, a small amount of DHPO in the solution containing CHPO obtained by the low temperature extraction, is mixed. Further, a small amount of CHPO in the solution containing DHPO obtained by the high temperature extraction, is also mixed. The CHPO and DHPO concentrations in the solution obtained by the low temperature extraction, are preferably controlled to 2 to 20% by weight and 1% by weight or less, respectively. In addition, the DHPO and CHPO concentrations in the solution obtained by the high temperature extraction, are preferably controlled to 5 to 30% by weight and 1% by weight or less, respectively.

The decomposition step (3) [herein-after, referred to as "decomposition step (I)] in the present invention is a step of obtaining a liquid containing a dihydroxybenzene by subjecting the liquid containing DHPO obtained in the separation step to decomposition reaction in the presence of an acid catalyst.

As the acid catalyst used in the decomposition step (I), there can be used Lewis acids such as aluminum chloride, trifluoro boron, ferric chloride and stannic chloride, and protic acids such as sulfuric acid, phosphorous acid, hydrochloric acid, perchloric acid, benzene sulfonic acid, p-toluene sulfonic acid and a strong acid ion exchange resin. From the viewpoint of yield and easy handling, concentrated sulfuric acid, sulfuric anhydride or fuming sulfuric acid is preferable and sulfuric anhydride is more preferable.

Since water of 1 to 10% by weight in the liquid to be subjected to the decomposition step (I) is usually contained, use as it is exerts a harmful influence on the acid catalyst for decomposition reaction. Therefore, concentration by which a part of the liquid is distilled off, is usually conducted before the decomposition step (I). By this concentration operation, water is also removed. It is preferable to dehydrate so that the water concentration decreases to 1% by weight or less. Thus obtained concentrated liquid is subjected to the decomposition step (I).

The decomposition step (I) is usually carried out under atmospheric pressure to a reduced pressure at a temperature of 30 to 150° C. for a reaction time of 1 to 200 minutes.

An acid decomposition reaction mixture obtained contains the acid catalyst and heavy components in addition to resorcinol (herein-after, referred to as "RES") or hydroquinone (herein-after, referred to as "HYQ"), acetone, and the organic solvent. RES or HYQ and acetone from the reaction mixture can be isolated via removal of the acid catalyst by an alkali neutralization and separation of liquids, removal of acetone and the organic solvent by distillation, and further, conventional operations such as distillation, extraction and crystallization.

The decomposition step (4) [herein-after, referred to as "decomposition step (II)"] is a step of obtaining a liquid containing acetone and isopropenyl phenol (herein-after, referred to as "OST") by subjection the liquid containing CHPO obtained in the separation step to decomposition reaction in the presence of an acid catalyst.

As the acid catalyst used in the decomposition step (II), there can be listed similar Lewis acids and protic acids to those used in the decomposition step (I). From the viewpoint of yield and easy handling, concentrated sulfuric acid, sulfuric anhydride or fuming sulfuric acid is preferable.

Since water of 1 to 10% by weight in the liquid to be subjected to the decomposition step (II) is usually contained, use as it is exerts a harmful influence on the acid catalyst for decomposition reaction. Therefore, concentration by which a part of the liquid is distilled off, is usually conducted before the decomposition step (II). By this concentration operation, water is also removed. It is preferable to remove so that the water concentration decreases to 1% by weight or less. Thus obtained concentrated liquid is subjected to the decomposition step (II).

The decomposition step (II) is usually carried out under atmospheric pressure to a reduced pressure at a temperature of 30 to 150° C. for a reaction time of 1 to 200 minutes.

An acid decomposition reaction mixture obtained contains the acid catalyst and heavy components in addition to OST, acetone and the organic solvent. Removal of the acid catalyst from the reaction mixture can be conducted by an alkali neutralization and separation of liquids (an oil layer and aqueous layer).

The distillation separation step (5) in the present invention is a step of separating into low boiling point components of acetone and the organic solvent, and heavy components containing OST by subjecting the organic solvent component containing OST and acetone obtained in the decomposition step (II) to a distillation operation.

The following apparatus and conditions for conducting this step, are exemplified, Conditions for distillation separation include a temperature of 100 to 200° C. and a pressure of 1 to 100 KPaA and as an apparatus, a distillation column is exemplified.

In addition, the heavy component containing OST separated may be employed, for example, as a part of a boiler fuel.

The reduction step (6) in the present invention, is a step of obtaining a liquid containing diisopropylbenzene dicarbinol (herein-after, referred to as "DCA") by subjecting a part of the liquid containing CHPO obtained in the separation step to reduction reaction.

Though DHPO and other impurities in the liquid to be subjected to reduction step, are contained in addition to CHPO, the liquid is subjected to reduction reaction as it is or after conducting a concentrating operation for which a part of the organic solvent is distilled away. The concentration of CHPO in the liquid is preferably 2 to 30% by weight.

As the reduction reaction, there can be applied a stoichiometric reduction using a reducing agent such as sodium sulfate or a reduction with hydrogen in the presence of a hydrogenation catalyst. Besides, the reduction with hydrogen in the presence of a hydrogenation catalyst, is preferable in industrial because it is better in a operability and lower in cost. As the hydrogenation catalyst, there can be used a conventional hydrogenation catalyst in which a noble metal of the group 8 of the Periodic Table of the Elements is supported on a support, and particularly, a palladium supported catalyst can be preferably used because of high activity and high selectivity. Examples of the support include alumina, silica, titania and magnesia. The supported concentration of palladium on the support is usually 0.01 to 10% by weight in terms of palladium metal. Hydrogen used for reduction may not be necessarily pure, and may contain an inert gas such as nitrogen, carbon dioxide or methane. The reaction pressure is usually 1 to 10 MPa, the reaction temperature is usually 20 to 150° C., the reaction time is usually 1 to 300 minutes. Though, as a reaction method, a flow reaction of a liquid phase in a fixed bed or a slurry reaction in a stirring vessel can be carried out, the slurry reaction in a stirring vessel using a powdery catalyst is suitable from the viewpoint of activity, selectivity and catalyst life. In a case of the slurry reaction in a stirring vessel, the catalyst concentration is usually within a range of 0.05 to 10% by weight.

The purification step (7) (herein-after, referred to as "post-treatment step") present invention, contains a step of purifying DCA from the reaction mixture containing DCA obtained in the reduction step through operations containing crystallization, filtration and drying and a step of supplying the filtrate obtained in the filtration to the decomposition step (II) and/or the distillation separation step.

DCA is purified from the reaction mixture containing DCA in the reduction step using operations of crystallization, filtration and drying. In addition, a concentration operation in which a part of the organic solvent is removed by distillation, may be carried out before the crystallization operation.

For example, the crystallization operation can selectively precipitate DCA crystals with cooling to 250° C. in a crystallization vessel under stirring.

The filtration operation is an operation for separating into DCA crystals and the organic solvent. Though vacuum filtration, pressure filtration, centrifugal filtration or the like is applied, centrifugal filtration is preferred from the viewpoint of operability. The filtrate obtained by the filtration contains DCA and the organic solvent, and can be supplied to the distillation separation step for recovering and reusing the organic solvent.

Further, when the amount of the filtrate supplied to the distillation separation step is too large, there are occurred problems that DCA contained in a boiler fuel obtained in the distillation separation step, precipitates and sending of the fuel to a boiler becomes impossible. Therefore, the filtrate is preferably sent to the decomposition step (II). In the decomposition step (II), diisopropenylbenzene (herein-after, referred to as "DST") can be obtained by subjecting DCA in the filtrate to decomposition reaction in the presence of an acid catalyst. Recovery of the organic solvent and prevention of the precipitation can be attained by supplying a liquid containing DST to the distillation separation step.

The drying operation is conducted for removing water and the organic solvent adhered to the DCA crystals obtained by the filtration to obtain a DCA product. The drying can be carried out under a pressure of 5 to 100 kPaA at a temperature of 20 to 100° C.

The greatest feature of the present invention is to recover and reuse an organic solvent without installing a new filtration recovery device by supplying the filtrate obtained by the filtration in the post-treatment step to the decomposition step (II) and/or the distillation separation step. In addition, though the filtrate is subjected to the distillation separation step and DCA as a heavy component is combustion-treated with a boiler, DCA in a boiler fuel precipitates when the amount of the filtrate is too large and sending of the fuel to a boiler becomes impossible. Therefore, according to the present invention, DCA in the filtrate converts into DST or the like by sending the filtrate in the decomposition step (II), whereby the precipitation in the boiler fuel can be prevented and the organic solvent can be efficiently recovered and used.

EXAMPLES

Next, the present invention will be described by Examples.

Example 1

An oxidation reaction was carried out by continuously feeding 60 parts by volume per hour of a raw material oil for oxidation containing a recycled component (containing 24% by weight of DIPB, 40% by weight of MHPO and 1% by weight of DHPO) to an oxidation reactor, continuously flowing 7000 parts by standard volume per hour of air through the reactor and controlling to a temperature of 90° C., a pressure of 0.3 MPa, a moisture of 3 to 4% by weight, a pH of 9 to 11 and a residence time of 10 hours. To this oxidation reaction mixture (liquid), 5 parts by volume per hour of DIPB solution was continuously fed to remove separated water and to obtain a reaction mixture containing a small amount of CHPO and the like in addition to 23.5% by weight of DIPB, 39% by weight of MHPO and 10% by weight of DHPO in the steady state. Countercurrent extraction (Extraction I) was carried out using 100 parts by weight of a mixed liquid (containing 13.5 by weight of DHPO and 1% by weight of CHPO) of a liquid obtained by extracting a oxidation product of DIPB with a 7 wt. % NaOH aqueous solution, with an aqueous solution (V) of DHPO after-described and 50 parts as a part of an MIBK solution (X) described after at a temperature of 35° C.

Thus obtained aqueous solution (W) after the extraction contained 12% by weight of DHPO and 0.1% by weight of CHPO.

Further, 99% of DHPO in the MIBK solution was recovered in an aqueous solution (V) by subjecting the MIBK solution after the Extraction I to countercurrent re-extraction (Extraction II) with 30 parts of a 7 wt. % NaOH aqueous solution at a temperature of 25° C. Furthermore, An MIBK solution (X) containing 12% by weight of DHPO, 0.1% by weight of CHPO and 3% by weight of water, was obtained by subjecting the an aqueous solution (W) after the Extraction I to extraction (Extraction III) with an excess amount of MIBK at 65° C. On the other hand, an MIBK solution (Y) containing 6% by weight of CHPO and 0.2% by weight of DHPO as the residue after recovering DHPO from the MIBK solution after Extraction I, was obtained.

A concentrated solution adjusted to 20% by weight of DHPO and 0.2% by weight of water by concentration of the MIBK solution (X) under reduced pressure, was subjected to acidolysis reaction. The reaction was carried out in the presence of 0.1% by weight of sulfur trioxide as a catalyst, under ordinary pressure at a reaction temperature of 70° C. for 10 minutes. The yield of RES based on DHPO, was 94%. Through rectification after the catalyst in the reaction mixture was removed by neutralization, acetone (purity: higher than 99%) and RES (purity: higher than 99%) could be isolated and further the MIBK as the solvent could be recovered.

A part of the MIBK solution (Y) as a raw material and 0.5% by weight of a palladium/alumina catalyst (1 wt. % of palladium in terms of palladium metal was supported on alumina) based on the raw material were present in a hydrogenation reactor equipped with an agitator, and a liquid phase hydrogen reduction was carried out under a hydrogen pressure of 0.5 MPa at a temperature of 98° C. for 60 minutes. The conversion of CHPO was substantially 100% and the concentration of DCA in the reaction mixture was 6% by weight. After the DCA concentration was adjusted to 20% by weight through concentration of the reaction mixture, and crystallization was carried out by lowering the temperature of the concentrate from 80° C. to 25° C. at a cooling speed of 0.25° C./minute. Thereafter, operations of filtration, MIBK washing and subsequent drying were carried out thereby to obtain DCA having a purity of higher than 99% at an isolated yield of 85%.

The residue liquid of the MIBK solution (Y) was concentrated under reduced pressure, and thus obtained concentrated solution having a CHPO concentration of 35% by weight and a water concentration of 0.1% by weight was subjected to acidolysis reaction. The reaction was carried out in the presence of concentrated sulfuric acid as a catalyst of 0.1% by weight under ordinary pressure at a temperature of 90° C. for 40 minutes, thereafter, a liquid containing OST (A) was obtained through a neutralization treatment. Acetone (purity: higher than 99%) and a boiler fuel were isolated, further MIBK as a solvent was recovered from the liquid containing OST (A) through rectification separation.

20 parts by weight of a filtrate (containing 75% by weight of MIBK and 4% by weight of DCA) generated by a filtration operation was mixed with 80 parts by weight of the liquid (A), and then, through rectification, DCA was isolated as a boiler oil and MIBK as a solvent was also recovered.

Example 2

The same operation was repeated except that the filtrate was subjected to decomposition together with the concentrated liquid (A) instead of subjecting the filtrate to rectification. A mixture of 47 parts by weight of the concentrated solution (Z) and 53 parts by weight of the filtrate was subjected to acidolysis reaction. The reaction was carried out in the presence of concentrated sulfuric acid as a catalyst of 0.1% by weight under ordinary pressure at a temperature of 90° C. for 40 minutes, thereafter, a liquid (A) containing OST and DST was obtained through a neutralization treatment. Through rectification separation of the liquid (A), acetone (purity: higher than 99%) and a boiler fuel were isolated whereby precipitation of DCA could be prevented, further MIBK as a solvent was recovered.

According to the present invention, there can be provided a process for simultaneously producing dihydroxybenzene and diisopropylbenzene dicarbinol using diisopropylbenzene as a raw material, which has an excellent effect such that a filtrate generated with production of diisopropylbenzene dicarbinol, can be efficiently treated.

The invention claimed is:

1. A process for simultaneously producing a dihydroxybenzene and a diisopropylbenzene dicarbinol, which comprises the following steps of:
   (1) oxidizing a diisopropylbenzene with an oxygen containing gas to obtain an oxidation reaction mixture containing a diisopropylbenzene dihydroperoxide and a diisopropylbenzene hydroxy hydroperoxide;
   (2) subjecting the oxidation reaction mixture obtained in the oxidation step (1) to extraction operation with an alkaline aqueous solution and to extraction operation with an organic solvent to separate into a liquid containing the diisopropylbenzene dihydroperoxide and a liquid containing the diisopropylbenzene hydroxy hydroperoxide;
   (3) subjecting the liquid containing the diisopropylbenzene dihydroperoxide to decomposition reaction in the presence of an acid catalyst to obtain a liquid containing a dihydroxybenzene;
   (4) subjecting the liquid containing the diisopropylbenzene hydroxy hydroperoxide to decomposition reaction in the presence of an acid catalyst to obtain a liquid containing acetone and an isopropenyl phenol;
   (5) subjecting the liquid containing acetone and the isopropenyl phenol to distillation to separate it into a mixture of acetone and the organic solvent, and a heavy fraction containing the isopropenyl phenol;
   (6) subjecting a part of the diisopropylbenzene hydroxy hydroperoxide to reduction reaction thereby to obtain a liquid containing a diisopropylbenzene dicarbinol; and
   (7) purifying the diisopropylbenzene dicarbinol from the liquid containing the diisopropylbenzene dicarbinol through purification operations containing crystallization, filtration and drying, and supplying a filtrate obtained by the filtration to the decomposition step (4) and/or distillation step (5).

2. The process according to claim 1, wherein the diisopropylbenzene is m-diisopropylbenzene and/or p-diisopropylbenzene, the dihydroxybenzene is resorcinol and/or hydroquinone and the diisopropylbenzene dicarbinol is m-diisopropylbenzene dicarbinol and/or p-diisopropylbenzene dicarbinol.

3. The process according to claim 1, wherein the diisopropylbenzene is m-diisopropylbenzene, the dihydroxybenzene is resorcinol and the diisopropylbenzene dicarbinol is m-diisopropylbenzene dicarbinol.

4. The process according to claim 1, wherein the alkaline aqueous solution used in the step (2) is a sodium hydroxide solution.

5. The process according to claim 1, wherein the solvent used for extraction in the step (2) is methylisobutylketone.

6. The process according to claim 1, wherein the acid catalysts used in the steps (3) and (4) are respectively concentrated sulfuric acid, sulfuric anhydride or fuming sulfuric acid.

* * * * *